(12) United States Patent
Kassab et al.

(10) Patent No.: US 11,395,677 B2
(45) Date of Patent: Jul. 26, 2022

(54) DEVICES, SYSTEMS, AND METHODS FOR USE WITH SUCTION WITHIN A MAMMALIAN BODY

(71) Applicants: Ghassan S. Kassab, La Jolla, CA (US); Zachary Berwick, San Diego, CA (US)

(72) Inventors: Ghassan S. Kassab, La Jolla, CA (US); Zachary Berwick, San Diego, CA (US)

(73) Assignee: CVDevices, LLC, San Diego, CA (US)

( * ) Notice: Subject to any disclaimer, the term of this patent is extended or adjusted under 35 U.S.C. 154(b) by 789 days.

(21) Appl. No.: 16/076,547

(22) PCT Filed: Feb. 9, 2017

(86) PCT No.: PCT/US2017/017178
§ 371 (c)(1),
(2) Date: Aug. 8, 2018

(87) PCT Pub. No.: WO2017/139463
PCT Pub. Date: Aug. 17, 2017

(65) Prior Publication Data
US 2019/0046236 A1 Feb. 14, 2019

Related U.S. Application Data

(60) Provisional application No. 62/380,344, filed on Aug. 26, 2016, provisional application No. 62/328,357, (Continued)

(51) Int. Cl.
*A61B 17/34* (2006.01)
*A61M 25/10* (2013.01)
(Continued)

(52) U.S. Cl.
CPC .......... *A61B 17/3478* (2013.01); *A61B 17/34* (2013.01); *A61M 25/10* (2013.01); *A61B 2017/00247* (2013.01); *A61B 2017/00986* (2013.01); *A61B 2017/306* (2013.01); *A61B 2017/308* (2013.01); *A61M 1/84* (2021.05);
(Continued)

(58) Field of Classification Search
CPC ......................... A61M 5/425; A61B 2017/308
See application file for complete search history.

(56) References Cited

U.S. PATENT DOCUMENTS 8,328,752 B2 12/2012 Kassab et al.
2004/0181237 A1* 9/2004 Forde ............... A61B 17/12122
623/1.11
(Continued)

OTHER PUBLICATIONS

International Searching Authority, International Search Report, PCT/US2017/017178, dated Jun. 28, 2017.
(Continued)

*Primary Examiner* — Jenna Zhang

(57) ABSTRACT

Devices, systems, and methods for use with suction within a mammalian body. In an exemplary embodiment of a device of the present disclosure, the device comprises one or more of the following: an inner tube, an outer tube, and a foldable portion, whereby movement of the two tubes relative to one another causes the foldable portion to form a suction cup, and conversely causes a suction cup to form a foldable portion, depending on the direction of relative movement.

12 Claims, 10 Drawing Sheets

Related U.S. Application Data filed on Apr. 27, 2016, provisional application No. 62/293,193, filed on Feb. 9, 2016.

(51) Int. Cl.

| | |
|---|---|
| *A61B 17/00* | (2006.01) |
| *A61B 17/30* | (2006.01) |
| *A61M 25/00* | (2006.01) |
| *A61M 25/04* | (2006.01) |
| *A61M 1/00* | (2006.01) |

(52) U.S. Cl.
CPC ......... *A61M 25/0074* (2013.01); *A61M 25/04* (2013.01)

(56) References Cited

U.S. PATENT DOCUMENTS

| | | | | |
|---|---|---|---|---|
| 2004/0260332 | A1* | 12/2004 | Dubrul | A61B 17/22 606/157 |
| 2005/0010197 | A1* | 1/2005 | Lau | A61M 1/80 606/1 |
| 2008/0009886 | A1 | 1/2008 | Self | |
| 2010/0030102 | A1* | 2/2010 | Poston | A61B 17/3401 600/561 |
| 2010/0081867 | A1* | 4/2010 | Fishler | A61F 2/2481 600/37 |
| 2010/0160719 | A1* | 6/2010 | Kassab | A61M 60/50 604/523 |
| 2010/0234838 | A1* | 9/2010 | Watson | A61M 25/1006 604/509 |
| 2011/0230706 | A1* | 9/2011 | Warren | A61B 17/00234 600/37 |
| 2012/0191181 | A1* | 7/2012 | Kassab | A61B 17/3478 623/2.11 |
| 2015/0133727 | A1 | 5/2015 | Bacich et al. | |
| 2016/0022293 | A1* | 1/2016 | Dubrul | A61B 17/11 606/194 |

OTHER PUBLICATIONS

International Searching Authority, Written Opinion of the International Searching Authority, PCT/US2017/017178, dated Jun. 28, 2017.

* cited by examiner

DEVICES, SYSTEMS, AND METHODS FOR USE WITH SUCTION WITHIN A MAMMALIAN BODY

PRIORITY

The present application is related to, claims the priority benefit of, and is a U.S. 35 U.S.C. 371 national stage patent application of, International Patent Application Serial No. PCT/US2017/017178, filed Feb. 9, 2017, which is related to, and claims the priority benefit of, U.S. Patent Application Ser. No. 62/380,344, filed Aug. 26, 2016, U.S. Patent Application Ser. No. 62/328,357, filed Apr. 27, 2016, and U.S. Patent Application Ser. No. 62/293,193, filed Feb. 9, 2016. The entire contents of these applications are also incorporated herein by reference. The contents of U.S. Pat. No. 8,328,752 of Kassab et al. are also expressly incorporated herein by reference.

BACKGROUND

Suctional engagement of tissues using a device, such as during an interventional procedure, is complex and requires small devices to accomplish the same. However, several devices currently used by medical practitioners either do not provide enough suctional engagement to perform a necessary procedure, or are too large to perform such a procedure. Effective devices and systems for use with suction to effectively engage tissues would be well received in the marketplace.

BRIEF SUMMARY

In an exemplary embodiment of a device of the present disclosure, the device comprises one or more of the following: an inner tube, an outer tube, and a foldable portion, whereby movement of the two tubes relative to one another causes the foldable portion to form a suction cup, and conversely causes a suction cup to form a foldable portion, depending on the direction of relative movement. Said devices, in various embodiments, are configured to deliver a liquid material, such as alginate, to a tissue of interest, such as cardiac tissue, to treat heart failure.

In at least one embodiment of a device of the present disclosure, the device comprises an outer tube positioned around an inner tube having at least one inner lumen defined therethrough, whereby the outer tube and the inner tube are connected together at a distal end of the device; and a foldable portion coupled to the outer tube; wherein movement of the outer tube relative to the inner tube in a first direction causes the foldable portion to fold, forming a suction cup at the distal end of the device. In at least one embodiment of a device of the present disclosure, the foldable portion comprises a plurality of flanges. In at least one embodiment of a device of the present disclosure, the plurality of flanges comprise a plurality of arcuate flanges. In at least one embodiment of a device of the present disclosure, a configuration of the plurality of flanges defines a configuration of the suction cup. In at least one embodiment of a device of the present disclosure, a distal tapered portion is present along the device between the foldable portion and the distal end of the device. In at least one embodiment of a device of the present disclosure, a proximal tapered portion is present along the device adjacent to the foldable portion. In at least one embodiment of a device of the present disclosure, the suction cup defines an interior environment having a larger cross-sectional area than a cross-section of the at least one inner lumen defined within the inner tube.

In at least one embodiment of a device of the present disclosure, movement of the outer tube relative to the inner tube in a second direction opposite the first direction causes the suction cup to fold so that the suction cup is no longer present. In at least one embodiment of a device of the present disclosure, the device forms part of a system, the system further comprising a sleeve positioned at least partially around the device, and/or a delivery catheter positioned at least partially within the at least one inner lumen of the device, and/or a needle positioned at least partially within the at least one inner lumen of the device, and/or a needle positioned at least partially within the delivery catheter, and/or a wire positioned at least partially within the needle. In at least one embodiment of a device of the present disclosure, the device is configured so that when foldable portion is folded to form the suction cup, suction through the at least one inner lumen of the device can cause the suction cup to suctionally engage a tissue or organ adjacent to the suction cup. In at least one embodiment of a device of the present disclosure, the at least one inner lumen comprises a single inner lumen, two inner lumens, three inner lumens, or four or more inner lumens.

In at least one embodiment of a device of the present disclosure, the device further comprises a first foldable bellow portion coupled to the outer tube proximal to the foldable portion, wherein movement of the outer tube relative to the inner tube in the first direction also causes the first foldable bellow portion to fold, forming a first bellow. In at least one embodiment of a device of the present disclosure, the first bellow portion comprises a plurality of flanges. In at least one embodiment of a device of the present disclosure, the plurality of flanges comprise a plurality of arcuate flanges. In at least one embodiment of a device of the present disclosure, the device further comprises a second foldable bellow portion coupled to the outer tube proximal to the first foldable portion, wherein movement of the outer tube relative to the inner tube in the first direction also causes the second foldable bellow portion to fold, forming a second bellow. In at least one embodiment of a device of the present disclosure, a distal tapered portion is present along the device between the foldable portion and the distal end of the device. In at least one embodiment of a device of the present disclosure, a proximal tapered portion is present along the device adjacent to the foldable portion. In at least one embodiment of a device of the present disclosure, the suction cup defines an interior environment having a larger cross-sectional area than a cross-section of the at least one inner lumen defined within the inner tube.

In at least one embodiment of a device of the present disclosure, movement of the outer tube relative to the inner tube in a second direction opposite the first direction causes the suction cup to fold so that the suction cup is no longer present. In at least one embodiment of a device of the present disclosure, movement of the outer tube relative to the inner tube in the second direction opposite the first direction causes the first foldable bellow portion fold so that the first bellow is no longer present. In at least one embodiment of a device of the present disclosure, the device forms part of a system, the system further comprising a sleeve positioned at least partially around the device, and/or a delivery catheter positioned at least partially within the at least one inner lumen of the device, and/or a needle positioned at least partially within the at least one inner lumen of the device, and/or a needle positioned at least partially within the delivery catheter, and/or a wire positioned at least partially within the needle. In at least one embodiment of a device of the present disclosure, the device is configured so that when foldable portion is folded to form the suction cup, suction through the at least one inner lumen of the device can cause the suction cup to suctionally engage a tissue or organ adjacent to the suction cup. In at least one embodiment of a device of the present disclosure, the at least one inner lumen comprises a single inner lumen, two inner lumens, three inner lumens, or four or more inner lumens. In at least one embodiment of a device of the present disclosure, the device comprises an outer tube defining at least one inner lumen therethrough; a compliant suction cup positioned at a distal end of the device; and a first bellow positioned between the outer tube and the compliant suction cup. In at least one embodiment of a device of the present disclosure, the device forms part of a system, the system further comprising a sleeve positioned at least partially around the device, and/or a delivery catheter positioned at least partially within the at least one inner lumen of the device, and/or a needle positioned at least partially within the at least one inner lumen of the device, and/or a needle positioned at least partially within the delivery catheter, and/or a wire positioned at least partially within the needle. In at least one embodiment of a device of the present disclosure, the device is configured so that suction through the at least one inner lumen of the device can cause the suction cup to suctionally engage a tissue or organ adjacent to the suction cup. In at least one embodiment of a device of the present disclosure, the device is configured so that suction through the at least one inner lumen of the device can cause the suction cup to collapse so that the first bellow collapses upon the suction cup. In at least one embodiment of a device of the present disclosure, the at least one inner lumen comprises a single inner lumen, two inner lumens, three inner lumens, or four or more inner lumens.

In at least one embodiment of a device of the present disclosure, the device comprises an outer tube defining at least one inner lumen therethrough, the outer tube having a notch or groove defined therein at or near a distal end of the outer tube; a balloon positioned at or near the distal end of the outer tube upon the notch or groove, the balloon configured for inflation via an inflation tube positioned relative to elongated body or defined within elongated body; wherein the balloon, upon inflation, is configured so that suction through the at least one inner lumen of the device can cause the inflated balloon to suctionally engage a tissue or organ adjacent to the inflated balloon. In at least one embodiment of a device of the present disclosure, the device further comprises a distal tube element positioned at the distal end of the outer tube distal to the balloon. In at least one embodiment of a device of the present disclosure, the inflated balloon has a donut shape, a funnel shape, or is configured as a bellow. In at least one embodiment of a device of the present disclosure, the balloon is inflatable by way of operating an inflation source coupled to the device. In at least one embodiment of a device of the present disclosure, the inflated balloon defines an interior environment having a larger cross-sectional area than a cross-section of the at least one inner lumen defined within the outer tube.

In at least one embodiment of a device of the present disclosure, the device forms part of a system, the system further comprising a sleeve positioned at least partially around the device, and/or a delivery catheter positioned at least partially within the at least one inner lumen of the device, and/or a needle positioned at least partially within the at least one inner lumen of the device, and/or a needle positioned at least partially within the delivery catheter, and/or a wire positioned at least partially within the needle. In at least one embodiment of a device of the present disclosure, the at least one inner lumen comprises a single inner lumen, two inner lumens, three inner lumens, or four or more inner lumens.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1:
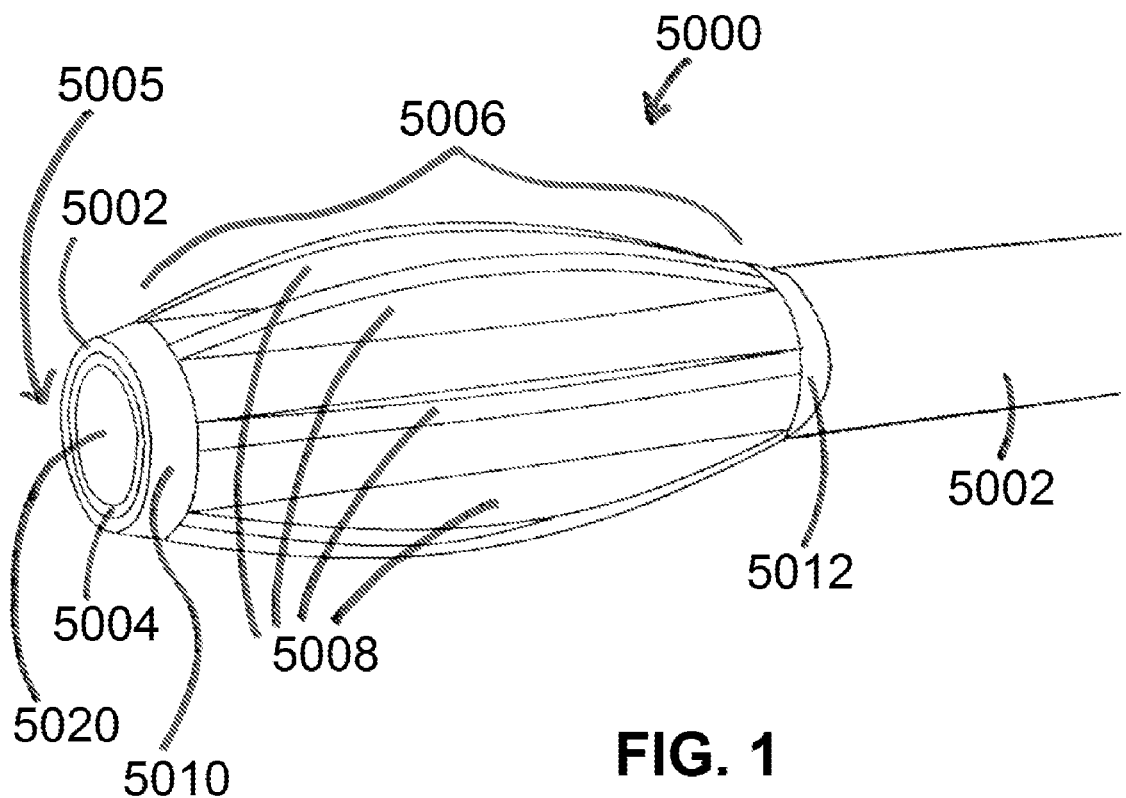
FIG. 1 shows a distal portion of a device configured to form a suction cup in a collapsed configuration, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure also includes disclosure of a device 5000 useful to facilitate various procedures within or upon a mammalian body or tissue. As shown in FIG. 1, a distal portion of device 500 is shown in a collapsed configuration, which comprises an outer tube 5002 positioned around an inner tube 5004, whereby outer tube 5002 and inner tube 5004 are connected together at a distal end 5005 of device 5000. Device 5000, in various embodiments, further comprises a foldable portion 5006 comprising an optional plurality of flanges 5008, such as arcuate flanges 5008 as shown in the figure. A distal tapered portion 5010 and a proximal tapered portion 5012 may also be included within various device 5000 embodiments.

Figure 2:
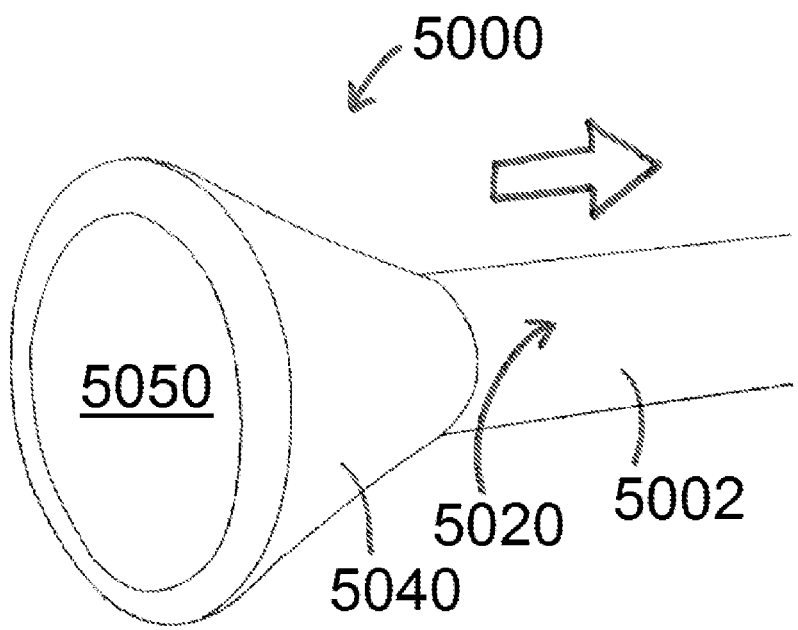
FIG. 2 shows a distal portion of a device configured to form a suction cup in an expanded configuration so to form a suction cup, according to an exemplary embodiment of the present disclosure.

Devices 5000 of the present disclosure are configured to form a suction cup as shown in the expanded configuration of device 5000 shown in FIG. 2, whereby suction cup 5040 is formed by way of relative movement of outer tube 5002 to inner tube 5004. An interior environment 5050, as shown in FIG. 2, is then formed within suction cup 5040. Movement of inner tube 5004 in a proximal direction (as identified by the arrow in FIG. 2) relative to outer tube causes the distal end 5005 of device to fold within itself, whereby distal end 5005 is pulled in the same proximal direction as identified by said arrow. Said movement causes portions of foldable portion 5006 to fold inward (at a now-defined distal end of device 5000), so to form suction cup 5040 as shown in FIG. 2. Device 5000 can be used similar to use of an engagement catheter 1810 of the present disclosure, whereby portions of delivery catheters 1840, needles 1890, wires 1895, etc., can be positioned within an inner lumen 5020 defined within device 5000 (namely the inside of inner tube 5004).

Figure 3:
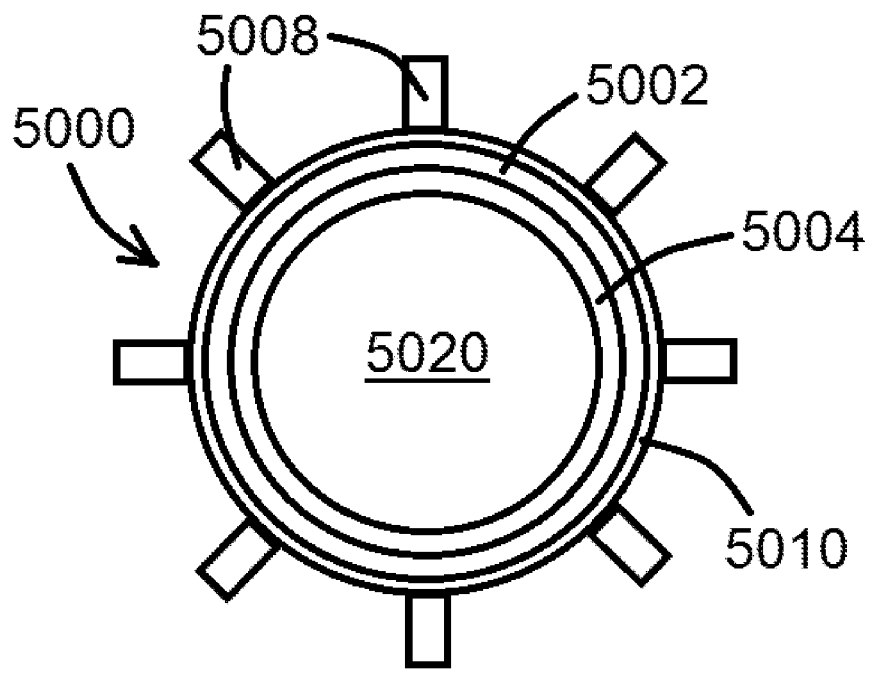
FIG. 3 shows a distal end view of a device configured to form a suction cup in a collapsed configuration, according to an exemplary embodiment of the present disclosure.
Figure 4:
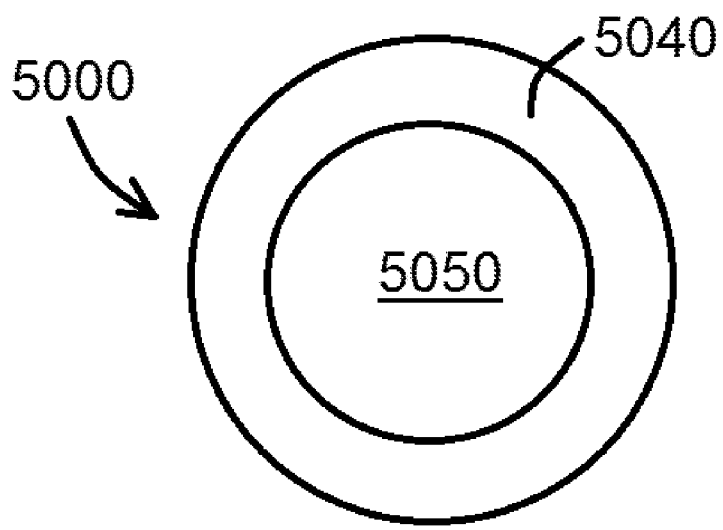
FIG. 4 shows a distal end view of a of a device configured to form a suction cup in an expanded configuration so to form a suction cup, according to an exemplary embodiment of the present disclosure.

Foldable portion 5006, so to be able to form suction cup 5040 (in the collapsed configuration shown in FIG. 2), convert back to foldable portion 5006 (as shown in the expanded configuration shown in FIG. 1), and back to suction cup 5040 (in any order), will comprise a material compliant enough to allow for such folding to occur but to also maintain the shape/integrity of suction cup 5040 when folded over. Flanges 5008, in at least one embodiment, allow for folding and the shape/integrity of suction cup 5040 as referenced herein. Inner tube 5002 and/or outer tube 5004, by way of contrast, may comprise a less compliant (more rigid) material so to allow for suction and/or delivery as referenced herein. Folding of portion 5006 can be adjusted to provide desired sizes and/or shapes of suction cups 5040 based on the degree to which inner tube 5004 is pulled within outer tube 5002 and/or the shape(s) of flanges 5008. The overall shape of suction cups 5040 can be provided by a less compliant material along without requiring flanges 5008 for support. Furthermore, the suction cup 5040 material can be extended to cover an entire movable section (an entire foldable portion 5006), such as shown in FIG. 1, or can extend partially from outer tuber 5002 to provide a desired suction cup 5040 depth and/or shape. FIGS. 3 and 4 show distal end views of embodiments of devices 5000 as described above. Device 5000, in various embodiments, can be considered as being a two-shaft catheter system where the inner, smaller diameter catheter (inner tube 5004) is attached to the distal end of the suction cup 5040 and the outer, larger diameter catheter (outer tube 5002) is attached to the proximal end of the suction cup 5040. Each catheter shaft can move independent of the other. In the collapsed configuration, the inner catheter is extended beyond the outer catheter. In the expanded configuration, the inner catheter is pulled back into the outer catheter causing the suction cup to expand. In various embodiments referenced above, movement of inner tube 5004 relative to outer tube 5002 causes suction cup 5040 to form and/or expand to form the effective foldable portion 5006, noting that folding of foldable portion 5006 is what causes suction cup 5040 to form.

Figure 5:
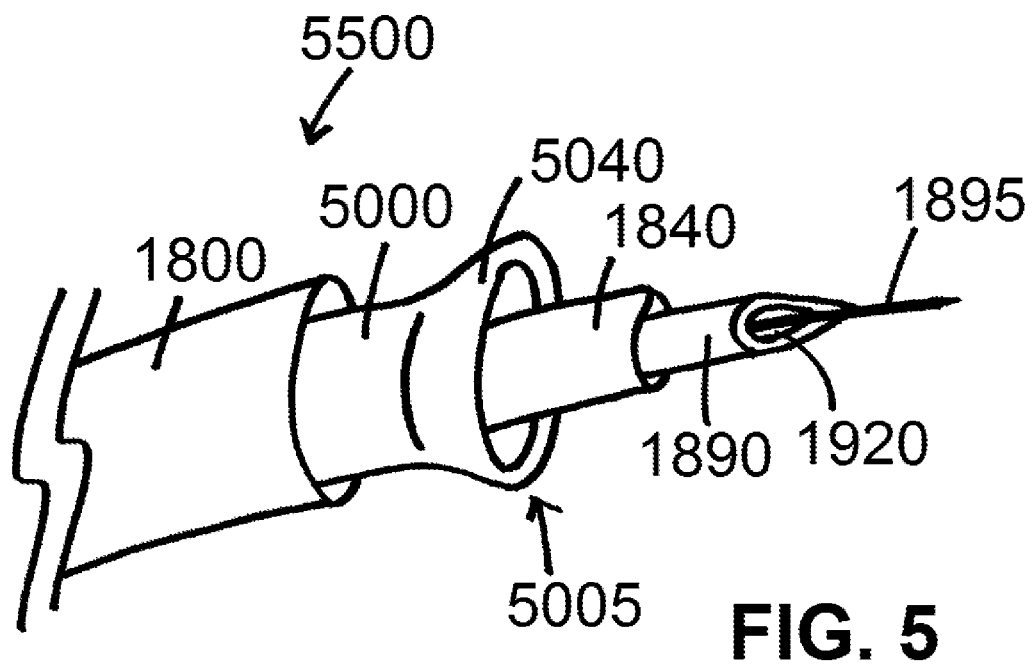
FIG. 5 shows a distal portion of system for isolating tissue and/or delivering a material, according to an exemplary embodiment of the present disclosure.
Figure 6:
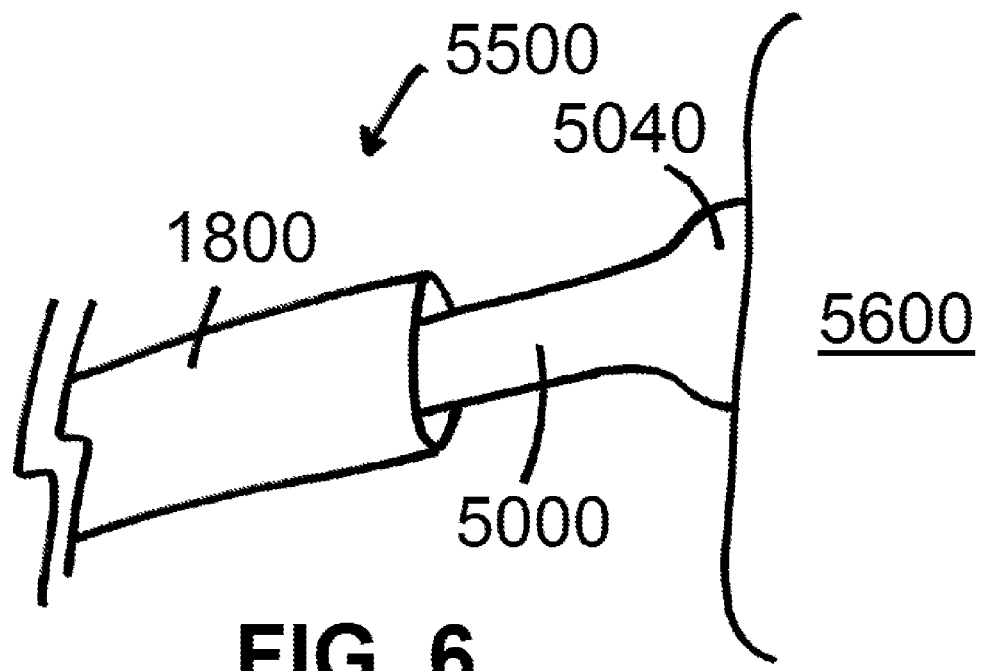
FIG. 6 shows a distal portion of a system suctionally affixed to a mammalian tissue, according to an exemplary embodiment of the present disclosure.
Figure 7:
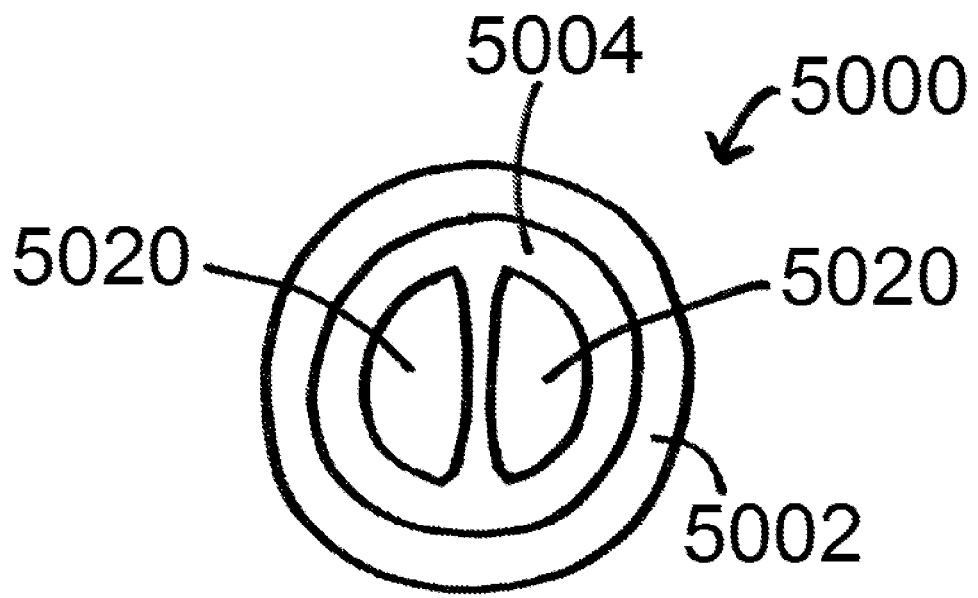
FIGS. 7 and 8 show distal end views of devices, according to exemplary embodiments of the present disclosure.
Figure 8:
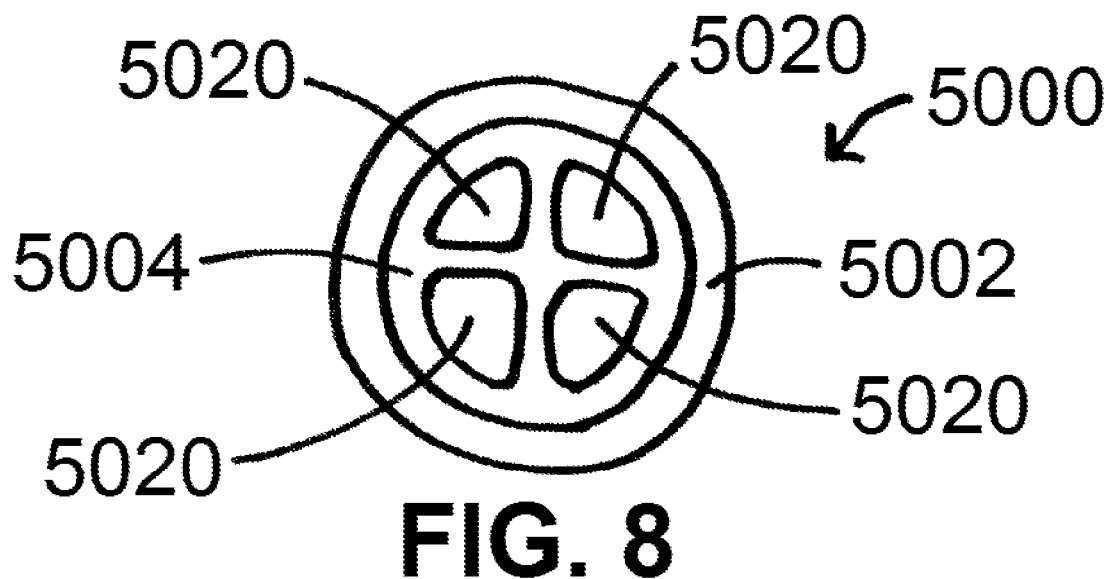

An exemplary system 5500 of the present disclosure is shown in FIG. 5. As shown in FIG. 5, distal portion of an exemplary system 5500 may comprise a device 5000 configured in an expanded configuration so to form a suction cup 5040, as referenced above, at a distal end 5005 of device 5000. System 5000 may further comprise a sleeve 1800 positioned around portions of device 5000 and configured for sliding movement relative to device 5000 such that movement of sleeve 1800 relative to device 5000 can cause suction cup 5040 to be within or external to sleeve 1800. System 5500 may further comprise a delivery catheter 1840 configured to fit within device 5000 and configured for sliding movement relative to device 5000. System 5500 may further comprise a needle 1890 defining a needle aperture 1920 and configured to fit within delivery catheter 1840 and/or device 5000 and configured for sliding movement relative to delivery catheter 1840 and/or device 5000. System 5500 may further comprise a wire 1895 configured to fit within device 5000, delivery catheter 1840, and/or needle 1890, and configured for sliding movement relative to device 5000, delivery catheter 1840, and/or needle 1890. Components of such exemplary system 5500 embodiments may be as described within U.S. Pat. No. 8,328,752 of Kassab et al., the contents of which are expressly incorporated herein by reference. FIG. 6 shows a distal portion of an exemplary system 5500 of the present disclosure, with system 5500 comprising a sleeve 1800 positioned at least partially around a device 5000 configured so to form the suction cup 5040 at a distal end 5005 of device 5000. Suction cup 5040 is shown as engaging a surface of a tissue or organ 5600 (which may be any number of mammalian tissues or organs, such as the skin, a heart, and the like, regardless or a presence of a lumen therein). Such engagement is provided via suction through device 5000. Suction can be provided as described within U.S. Pat. No. 8,328,752 of Kassab et al., noting that various portions of devices and/or systems disclosed within U.S. Pat. No. 8,328,752 of Kassab et al. may be used in connection with devices 5000 and/or systems 5500 of the present disclosure. Various device 5000 embodiments can comprise an inner tube 5004 defining one or more internal lumens 5020 therein. In various embodiments, inner tubes 5004 of the present disclosure may comprise one lumen 5020, as shown in FIG. 1, two internal lumens 5020 as shown in the distal end view of device 5000 shown in FIG. 7, three internal lumens 5020 (not shown), four internal lumens 5020 as shown in the distal end view of device 5000 shown in FIG. 8, or five or more internal lumens 5020. Devices 5000 with multiple lumens 5020 can allow for vacuum, injection, or combinations thereof, as may be required/desired for attachment and delivery of substances, drugs, inert materials, etc., as may be referenced herein, for example.

Figure 9:
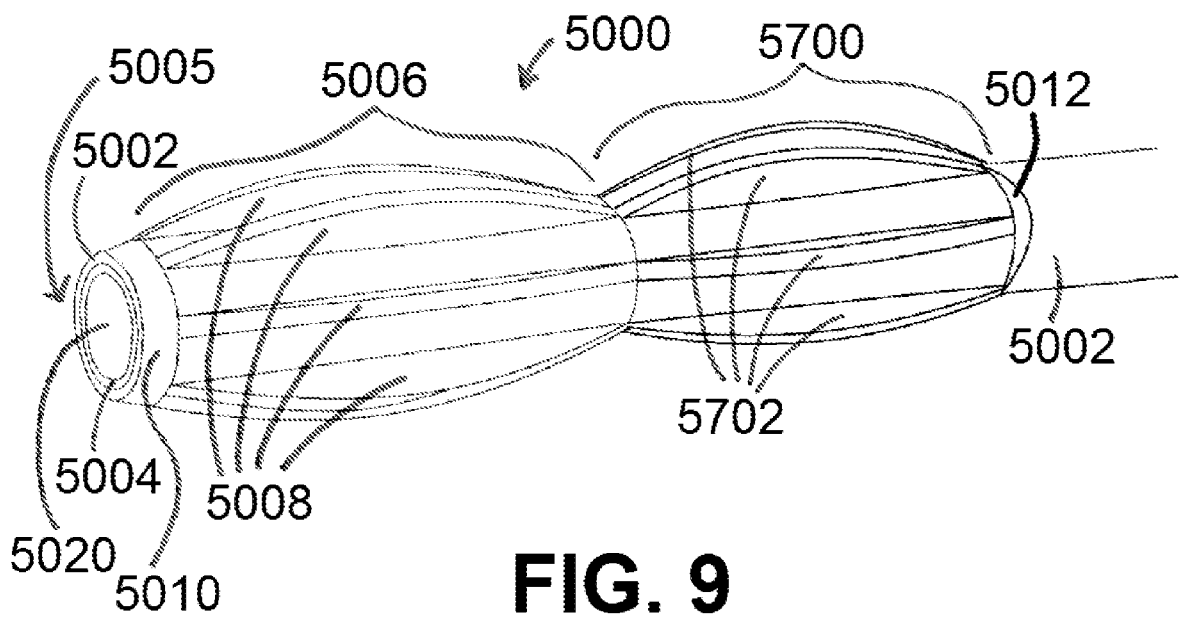
FIG. 9 shows a side perspective view of a distal portion of a device having a foldable portion (configured to fold to form a suction cup) and a foldable bellow portion, in an expanded or unfolded configuration, according to an exemplary embodiment of the present disclosure.
Figure 10:
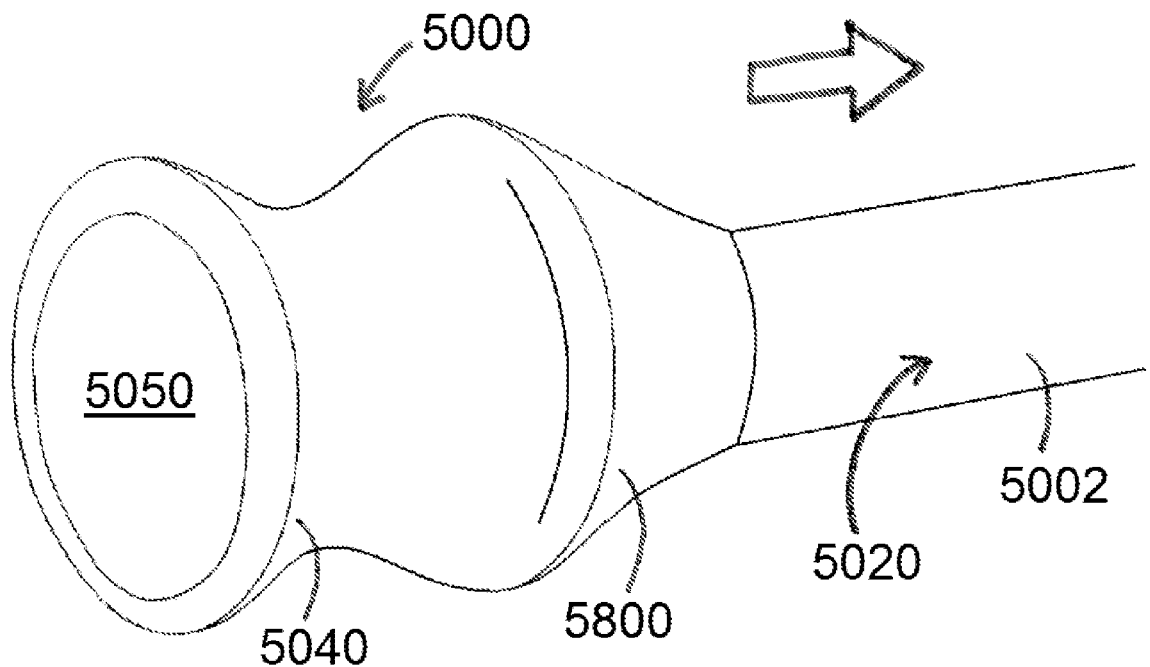
FIG. 10 shows a side perspective view of the device of FIG. 9 in a folded configuration so to form a suction cup and a bellow, according to an exemplary embodiment of the present disclosure.

FIGS. 9 and 10 show an additional embodiment of a device 5000 of the present disclosure. As shown therein, a distal portion of device 500 is shown in a collapsed configuration, which comprises an outer tube 5002 positioned around an inner tube 5004, whereby outer tube 5002 and inner tube 5004 are connected together at a distal end 5005 of device 5000, similar to that as shown in FIG. 1. Device 5000, in various embodiments, further comprises a foldable portion 5006 comprising an optional plurality of flanges 5008, such as arcuate flanges 5008 as shown in the figure. A distal tapered portion 5010 and a proximal tapered portion 5012 may also be included within various device 5000 embodiments. The device 5000 embodiments shown in FIGS. 9 and 10 also include a foldable bellow portion 5700, as shown in FIG. 9. Foldable bellow portion 5700, as shown in FIG. 9, may comprise an optional plurality of bellow flanges 5702, such as arcuate bellow flanges 5702 as shown in the figure. Devices 5000 of the present disclosure are configured to form a suction cup as shown in the expanded configuration of device 5000 shown in FIG. 9, whereby suction cup 5040 is formed by way of relative movement of outer tube 5002 to inner tube 5004. An interior environment 5050, as shown in FIG. 9, is then formed within suction cup 5040. Movement of inner tube 5004 in a proximal direction (as identified by the arrow in FIG. 2) relative to outer tube causes the distal end 5005 of device to fold within itself, whereby distal end 5005 is pulled in the same proximal direction as identified by said arrow. Said movement causes portions of foldable portion 5006 to fold inward (at a now-defined distal end of device 5000), so to form suction cup 5040 as shown in FIG. 9. Said movement also causes portions of foldable bellow portion 5700 to fold inward, so to form a bellow 5800, as shown in FIG. 10. Bellow 5800, as shown in FIG. 10, is proximal to suction cup 5040. FIGS. 9 and 10 show one foldable bellow portion 5700 and one bellow 5800, respectively, but in various other device 5000 embodiments, two, three, or more bellow portions 5700, corresponding to two, three, or more bellows 5800 when folded, may be present.

Foldable portion 5006, so to be able to form suction cup 5040, and foldable bellow portion 5700, so to be able to form bellow 5800 (in the collapsed configuration shown in FIG. 10), convert back to foldable portion 5006 and foldable bellow portion 5700 (as shown in the expanded configuration shown in FIG. 9), and back to suction cup 5040 and bellow 5800 (in any order), will comprise a material compliant enough to allow for such folding to occur but to also maintain the shape/integrity of suction cup 5040 and bellow 5800 when folded over. Flanges 5008 and 5702, in at least one embodiment, allow for folding and the shape/integrity of suction cup 5040 and bellow 5800 as referenced herein. Inner tube 5002 and/or outer tube 5004, by way of contrast, may comprise a less compliant (more rigid) material so to allow for suction and/or delivery as referenced herein.

Figure 11:
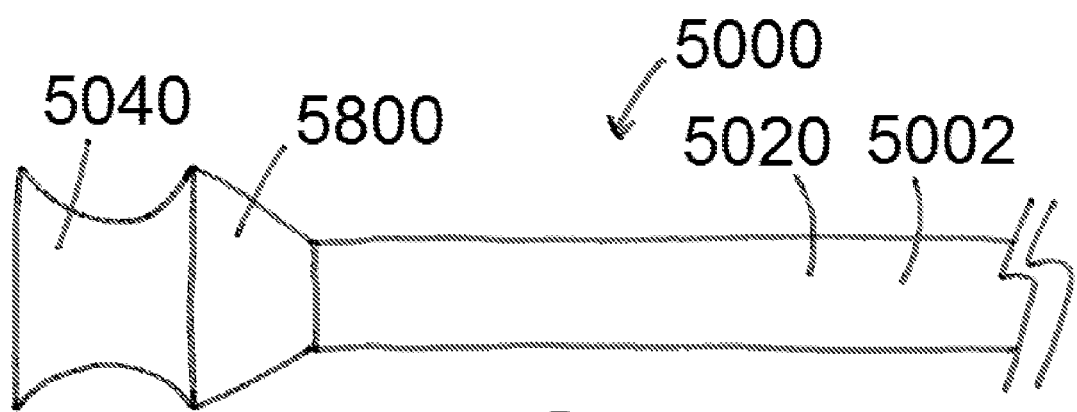
FIG. 11 shows a side view of a device having a suction cup and a bellow, according to an exemplary embodiment of the present disclosure.
Figure 12:
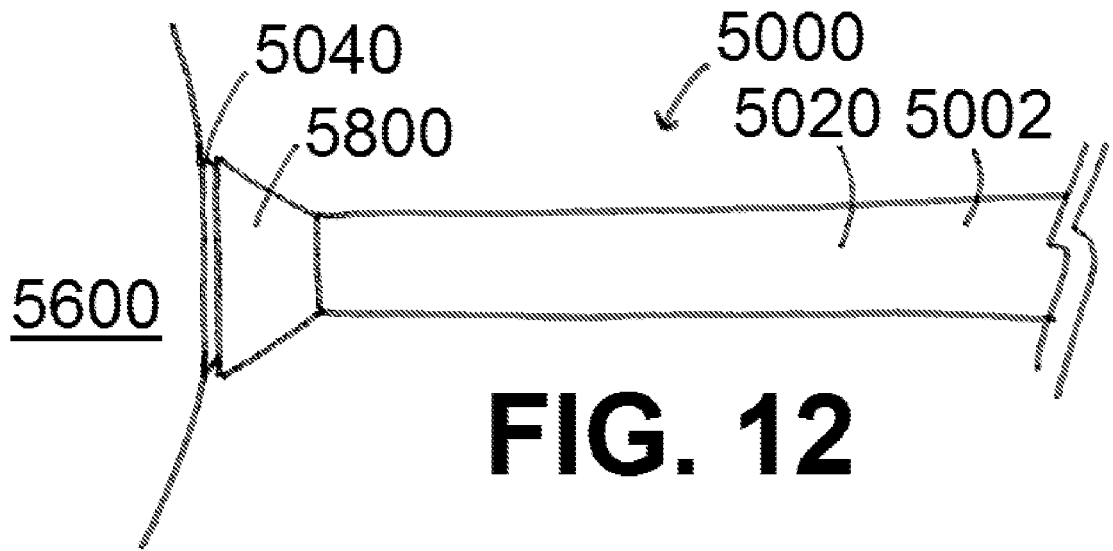
FIG. 12 shows a side view of a device whereby the bellow is folded about/upon the suction cup under suctional attachment to a tissue, according to an exemplary embodiment of the present disclosure.

An additional device 5000 embodiment of the present disclosure is shown in FIGS. 10 and 11. As shown therein, devices 5000 comprise a suction cup 5040 and at least one bellow 5800 proximal to said suction cup 5040, similar to as shown in FIG. 10. Suction cup 5040 and bellow 5800 are configured so that when no vacuum is applied through device 5000 (meaning here that there is no meaningful vacuum present within device 5000), bellow 5800 remains expanded, as shown in FIG. 11, and when vacuum is applied through device 5000 (meaning here that there is meaningful vacuum present within device 5000, such as when suction cup 5040 is suctionally attached to a targeted tissue 5600), bellow 5800 collapses about/upon suction cup 5040, as shown in FIG. 12. In view of the foregoing, the present disclosure includes disclosure of a suction engagement catheter (an exemplary device) having one, two, three, or more bellows 5800 proximal to a distal suction cup 5040, whereby, during application of suction and tissue engagement, the one, two, or three or more bellows 5800 collapse about one other.

Figure 13:
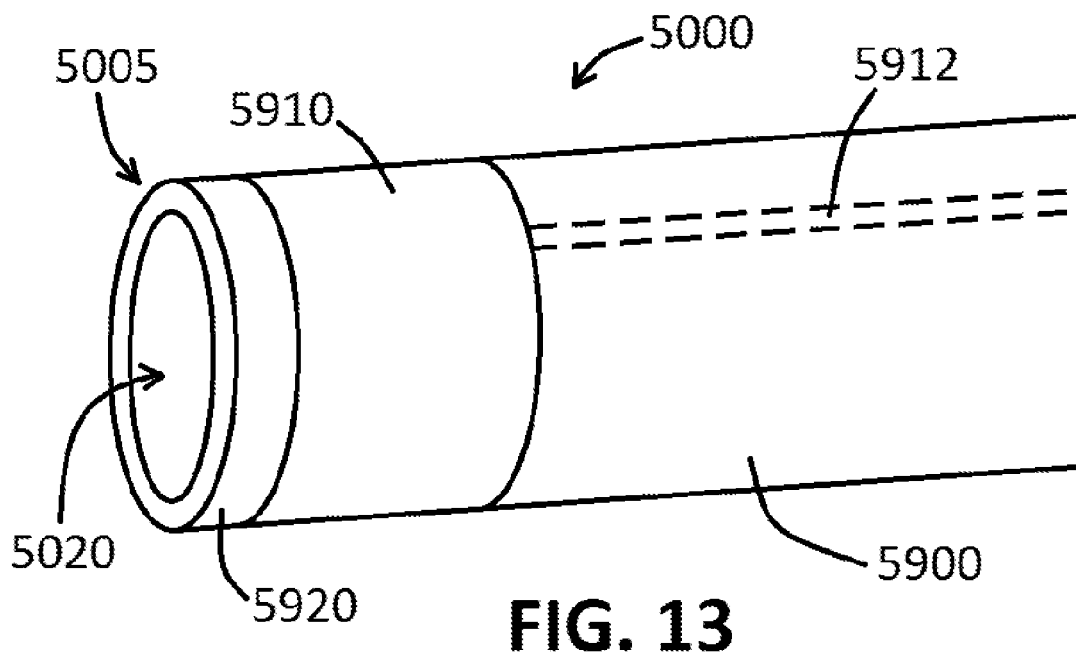
FIGS. 13 and 14 show perspective views of devices having a balloon in a deflated state, according to exemplary embodiments of the present disclosure.
Figure 14:
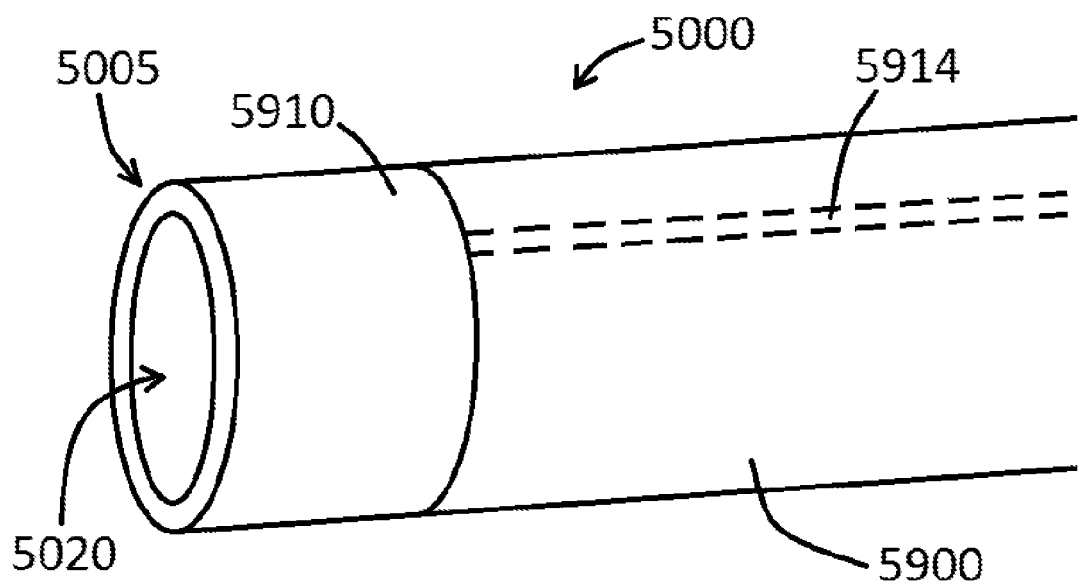
Figure 15:
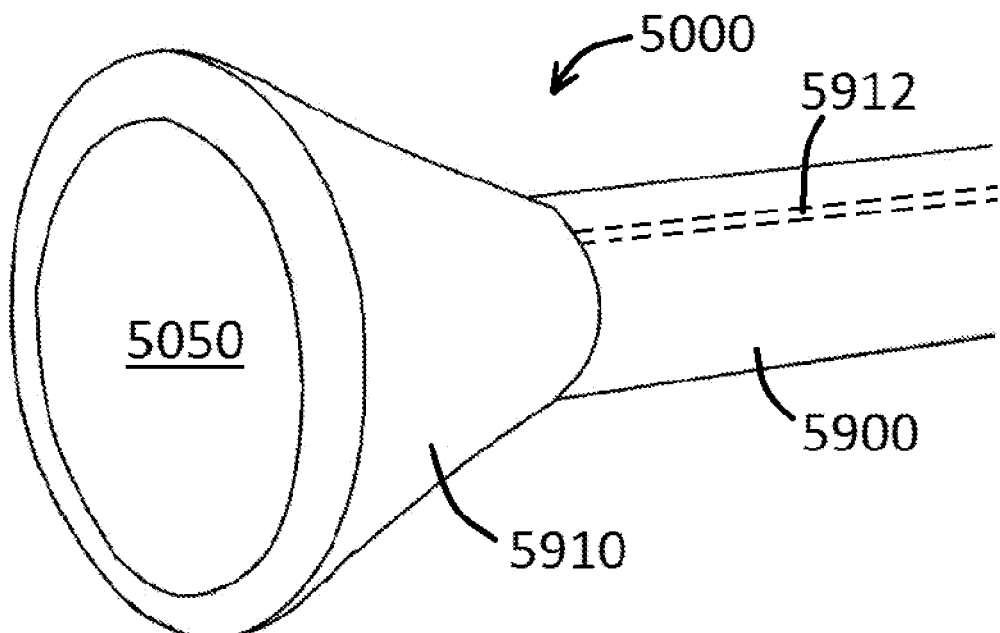
FIG. 15 shows a perspective view of a device having a balloon shaped as a funnel in an inflated state, according to an exemplary embodiment of the present disclosure.
Figure 16:
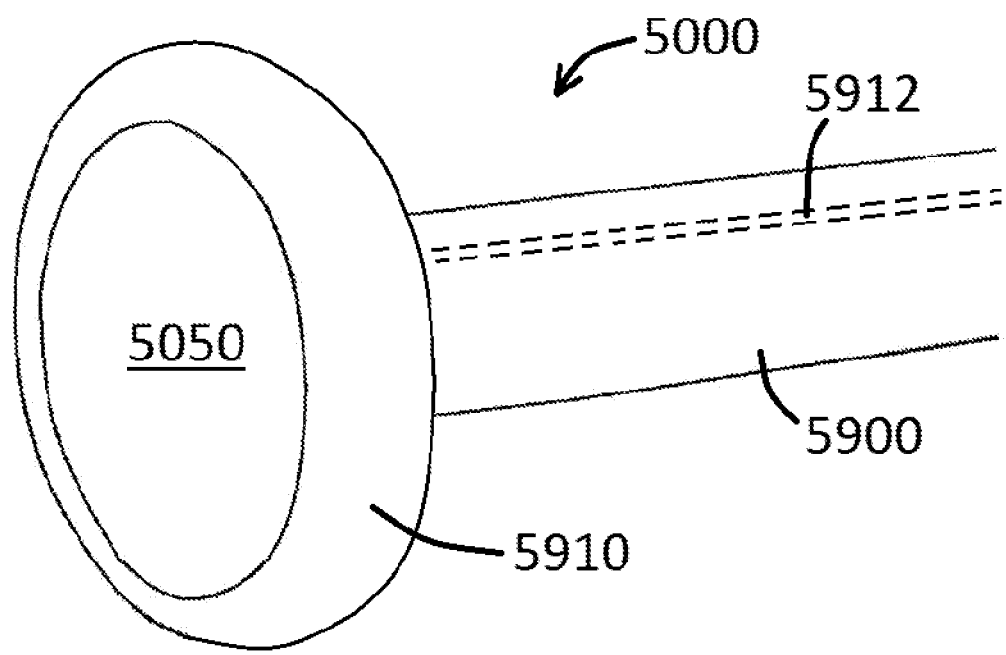
FIG. 16 shows a perspective view of a device having a balloon shaped as a donut in an inflated state, according to an exemplary embodiment of the present disclosure.
Figure 19:
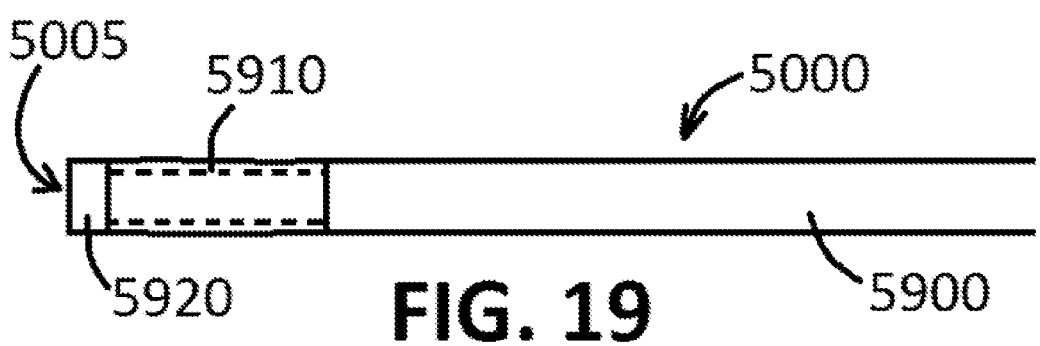

FIG. 13 shows an additional embodiment of a device 5000 of the present disclosure. As shown therein. Device 5000 comprises an elongated body 5900 configured as a catheter, whereby elongated body 5900, in various embodiments, could comprise outer tube 5900. Device 5000, as shown in FIG. 13, comprises a balloon 5910 positioned at or near a distal end 5005 of device. Balloon 5910, as shown in FIG. 13, is positioned along device 5000 proximal to distal end 5005, whereby a distal tube element 5920 is present between distal end 5005 and the rest of elongated body 5000. In other embodiments, such as shown in FIG. 14, balloon 5900 is positioned along device 5000 at distal end 5005 of device, such that no distal tube element 5920 is present. Balloon 5910, as shown in FIG. 13, is configured for inflation via an inflation port 5912 defined within elongated body 5900, or as shown in FIG. 14, via an inflation tube 5914 positioned relative to elongated body 5900. Balloon 5910, in an inflated state (such as shown in FIGS. 15 and 16), can have a funnel shape, such as shown in FIG. 15, or a donut shape, such as shown in FIG. 16, for example. Balloon 5910 can also be configured as a bellow 5800, such as shown in FIG. 10, upon inflation. Inflation of balloon 5910 can occur by way of operating an inflation source 6102 coupled to device 5000, such as to supply a gas and/or a liquid to inflate balloon 5910, via inflation port 5912 or inflation tube 5914 in communication with inflation source. Balloon 5910, when inflated, defines an interior environment 5050, whereby at least part of interior environment 5050 is sized so to have a diameter larger than a diameter of device 5000 or to have a cross-sectional area larger than a cross-sectional area of device 500. For example, and as shown in the end view of device 5000 shown in FIG. 19, inflated balloon 5910 has a distal opening having an inner diameter D1, as shown in the figure, while elongated body 5900 (configured as a tube, for example) has an inner diameter D2, as shown in the figure. D1, as shown in FIG. 19, is larger than D2. Use of such a device 5000, such as to engage a tissue or organ 5600, allows for a larger surface area of tissue or organ 5600 contact as compared to potential tissue contact with only elongated body 5900, when suction (vacuum) is applied through lumen 5020 of device, as referenced herein. The engagement of the larger surface area of the tissue or organ 5600 under vacuum allows device 5000 to better adhere to said tissue or organ 5600 under vacuum.

Figure 17:
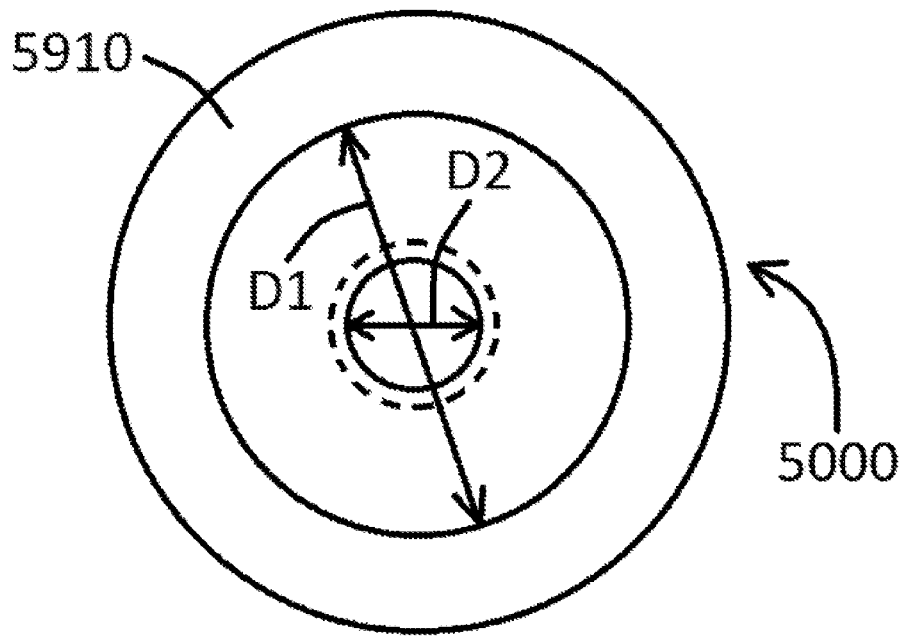
FIG. 17 shows an end view of a device having a balloon in an inflated state, according to an exemplary embodiment of the present disclosure.
Figure 18:
FIGS. 18, 19, 20, and 21 show side views of devices having a notch or groove defined therein, according to exemplary embodiments of the present disclosure.
Figure 20:
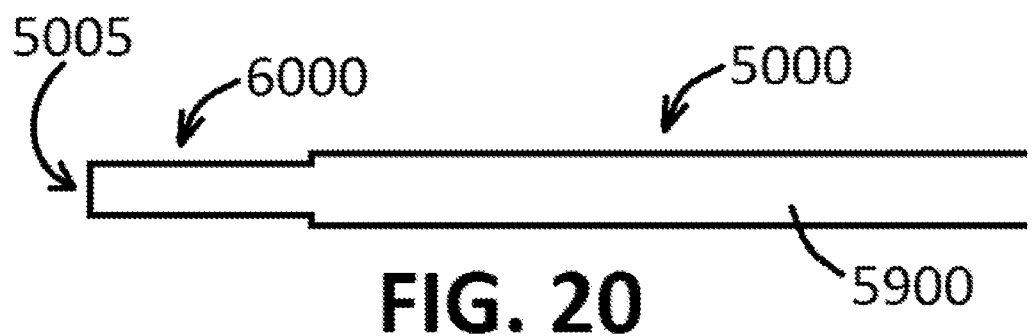
Figure 21:
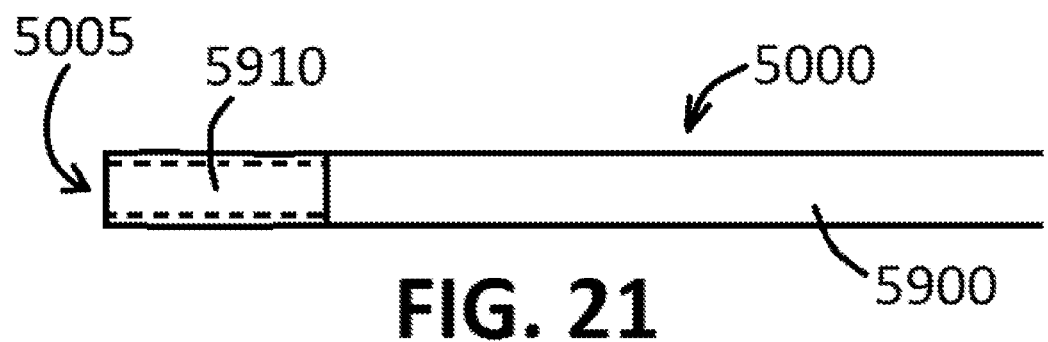

FIG. 18 shows an exemplary side view of a distal portion of a device 5000 of the present disclosure. As shown therein, a notch or groove 6000 is defined within elongated body at or near distal end 5005, whereby balloon 5910 can be positioned at notch or groove 6000, such as shown in FIG. 19. Balloon 5910, in a deflated state, allows device 5000 to be delivered via the vascular system as desired, and inflation of balloon 5910, such as shown in FIGS. 15, 16, and 17, provides for a larger cross-sectional area for tissue or organ 5600 engagement under vacuum, as referenced herein. Notch or groove 6000 can be defined within elongated body 5900 near distal end 5005 of device 5000, such as shown in FIGS. 18 and 19, or can be defined at distal end 5005 of device 5000, such as shown in FIGS. 20 and 21. Devices 5000, as referenced herein, can be exemplary engagement catheters 1810 of the present disclosure, as devices 5000 can be used to attach to a targeted tissue or organ 5600 under vacuum, as referenced herein and as shown in FIG. 6, for example.

Figure 22:
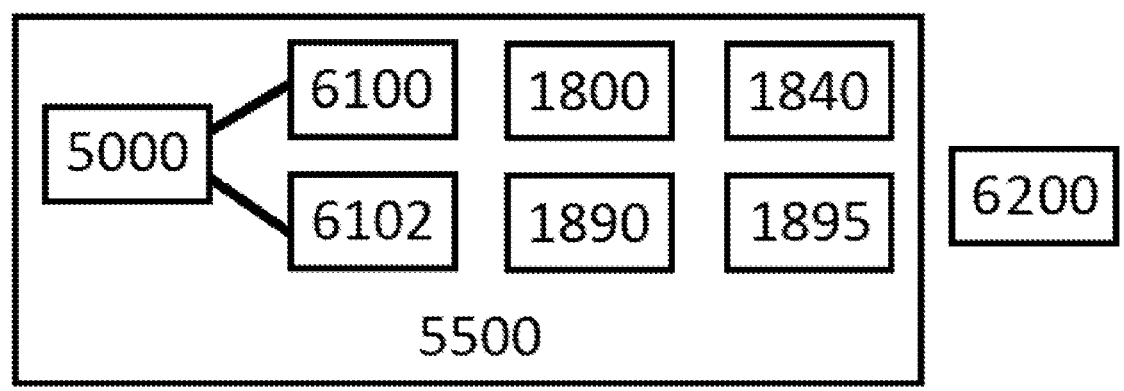
FIG. 22 shows a block component diagram of a system, according to an exemplary embodiment of the present disclosure.

FIG. 22 shows a block component diagram of an exemplary system 5500 of the present disclosure. As shown therein, system 5500 comprises an exemplary device 5000 of the present disclosure, coupled to a vacuum source 6100 (configured to generate a vacuum within lumen 5020 of device 5000 to facilitate suction engagement to a tissue or organ 5600), and also coupled to an inflation source 6102 (configured to inflate balloon 5910 using a gas and/or a liquid). Systems 5500 can include one or both of vacuum source 6100 and/or inflation source 6102, and can include/comprise one or more of a sleeve 1800, a delivery catheter 1840, a needle 1890, and/or a wire 1895, as shown and/or described herein. In various device 5000 embodiments, the one or more bellows 5800 provide articulation to device 500, such as to, for example, allow a device 5000 configured as a catheter to be better controlled during intravascular navigation, for example, as well as to provide for a more accurate and controlled delivery of a needle 1890 and/or media (such as one or more materials referenced herein).

Procedurally, portions of devices 5000 and/or systems 5500 can be delivered subendocardially, such as by way of needle puncture, so that suction cup 5500 is ultimately positioned against tissue or organ 5600 as desired. Various devices 5000 and/or portions of systems 1805 of the present disclosure can be delivered intravascularly, via thoracic puncture, etc., for ultimate use within the body, or can be used external to the body, such as upon the skin. Devices 5000 and/or systems 5500 can be used as follows, by way of example: a) to suctionally engage a tissue or organ 5600 so to stabilize said tissue or organ 5600; and/or b) to suctionally engage a tissue or organ 5600 so to directly deliver an item 6200 such as, for example, a medicament, such as a pharmaceutical compound (a drug), an injectable material, such as a polymer, a lead, cells, a coil, and/or another medical device; and/or c) to suctionally engage a tissue or organ 5600 so to facilitate delivery of a delivery catheter 1840, a needle 1890, and/or a wire 1920 through device 5000, whereby said delivery catheter 1840 and/or needle 1890 can be used to deliver an item 6200 such as, for example, a medicament, such as a pharmaceutical compound, an injectable material, a lead, a coil, and/or another medical device, and/or whereby wire 1920 can be used to guide portions of device 5000 and/or system 5500 within the body. Other uses of exemplary devices 5000 and/or systems 5500 are also contemplated herein and within the present disclosure, such as during known or developed medical procedures whereby suction engagement of a catheter to a tissue or organ 5600 is part of the procedure.

While various embodiments of devices and systems for use with suction within a mammalian body and methods for using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof. Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device, comprising:
an outer tube positioned around an inner tube having at least one inner lumen defined therethrough, whereby the outer tube and the inner tube are connected together at a distal end of the device;
a foldable portion coupled to the outer tube;
wherein movement of the outer tube relative to the inner tube in a first direction causes the foldable portion to fold, forming a suction cup at the distal end of the device; and
a first foldable bellow portion coupled to the outer tube proximal to the foldable portion;
wherein movement of the outer tube relative to the inner tube in the first direction also causes the first foldable bellow portion to fold, forming a first bellow.

2. The device of claim 1, wherein the foldable portion comprises a plurality of flanges.

3. The device of claim 1, wherein a configuration of the plurality of flanges defines a configuration of the suction cup.

4. The device of claim 1, wherein a distal tapered portion is present along the device between the foldable portion and the distal end of the device.

5. The device of claim 1, wherein a proximal tapered portion is present along the device adjacent to the foldable portion.

6. The device of claim 1, wherein the suction cup defines an interior environment having a larger cross-sectional area than a cross-section of the at least one inner lumen defined within the inner tube.

7. The device of claim 1, wherein movement of the outer tube relative to the inner tube in a second direction opposite the first direction causes the suction cup to fold so that the suction cup is no longer present.

8. The device of claim 1, wherein the first foldable bellow portion comprises a plurality of flanges.

9. The device of claim 1, further comprising:
a second foldable bellow portion coupled to the outer tube proximal to the first foldable bellow portion;
wherein movement of the outer tube relative to the inner tube in the first direction also causes the second foldable bellow portion to fold, forming a second bellow.

10. The device of claim 1, wherein movement of the outer tube relative to the inner tube in a second direction opposite the first direction causes the first foldable bellow portion fold so that the first bellow is no longer present.

11. A device, comprising:
an outer tube defining at least one inner lumen therethrough;
a compliant suction cup positioned at a distal end of the device; and
a first bellow positioned between the outer tube and the compliant suction cup;
wherein the device is configured so that suction being applied through the at least one inner lumen of the device can cause the suction cup to collapse so that the first bellow collapses upon the suction cup.

12. The device of claim 11, configured so that suction being applied through the at least one inner lumen of the device can cause the suction cup to suctionally engage a tissue or an organ adjacent to the suction cup.

* * * * *